United States Patent

Naoi et al.

[11] Patent Number: 5,164,087
[45] Date of Patent: Nov. 17, 1992

[54] LEUKOCYTE SEPARATOR

[75] Inventors: Keiji Naoi; Katsuhiko Iwata; Osamu Kaneko, all of Fuji, Japan

[73] Assignee: Terumo Kabushiki Kaisha, Tokyo, Japan

[21] Appl. No.: 647,198

[22] Filed: Jan. 28, 1991

Related U.S. Application Data

[63] Continuation of Ser. No. 317,867, Mar. 2, 1989, abandoned.

[30] Foreign Application Priority Data

Mar. 3, 1988 [JP] Japan .................. 63-50173
Mar. 3, 1988 [JP] Japan .................. 63-50174

[51] Int. Cl.$^5$ .................. B01D 39/00; B01D 63/00
[52] U.S. Cl. .................. 210/500.1; 210/496; 210/500.21; 210/500.42
[58] Field of Search .............. 210/496, 500.21, 500.42, 210/507, 508, 509, 500.26, 500.27, 500.1, 500.43, 500.35, 500.36, 500.37, 500.38, 500.4, 500.41

[56] References Cited

U.S. PATENT DOCUMENTS

| | | |
|---|---|---|
| 3,663,470 | 5/1972 | Nishimura .................. 260/2.5 F |
| 3,765,536 | 10/1973 | Rosenberg .................. 210/446 |
| 3,892,236 | 7/1975 | Djerassi . |
| 4,247,498 | 1/1981 | Castro .................. 264/41 |
| 4,330,410 | 5/1982 | Takenaka et al. .................. 210/767 |
| 4,416,777 | 11/1983 | Kuroda et al. .................. 210/509 |
| 4,490,431 | 12/1984 | Vitzthum et al. .................. 428/220 |
| 4,731,260 | 3/1988 | Balding et al. .................. 210/500.36 |
| 4,844,809 | 7/1989 | Ashina et al. .................. 210/636 |
| 4,845,132 | 7/1989 | Masuoka et al. .................. 521/53 |

FOREIGN PATENT DOCUMENTS

| | | |
|---|---|---|
| 0155003 | 9/1985 | European Pat. Off. . |
| 0188068 | 7/1986 | European Pat. Off. . |
| 0266683 | 5/1988 | European Pat. Off. . |
| 48-20019 | 6/1973 | Japan . |
| 58-38183 | 8/1983 | Japan . |
| 58-180425 | 10/1983 | Japan . |
| 59-6231 | 1/1984 | Japan . |
| 60-248203 | 12/1985 | Japan . |
| 61-39060 | 9/1986 | Japan . |
| 61-242687 | 10/1986 | Japan . |
| 62-97603 | 5/1987 | Japan . |
| 2056301 | 3/1981 | United Kingdom . |

OTHER PUBLICATIONS

The New England Journal of Medicine, vol. 265, No. 15, pp. 728-733, dated Oct. 12, 1961.
"Laboratory Filtration Microbiology Electrophoresis", Sartorius Membrane Filters, pp. 29-37.
Membrane Filters, published by Sartorius GmbH.

Primary Examiner—Robert A. Dawson
Assistant Examiner—Sun Uk Kim
Attorney, Agent, or Firm—Burns, Doane, Swecker & Mathis

[57] ABSTRACT

A leukocyte separator for trapping and separating leukocytes from blood is made of a porous material having a bubble point ranging from 0.08 to 0.3 kg/cm$^2$ and a thickness of at least 0.30 mm. The leukocyte separator is manufactured by pressing a porous material having a bubble point smaller than 0.13 kg/cm$^2$ to produce a porous material having a thickness of at least 0.3 mm and a bubble point ranging from 0.13 to 0.3 kg/cm$^2$.

7 Claims, 2 Drawing Sheets

LEUKOCYTE SEPARATOR

This application is a continuation of application Ser. No. 07/317,867, filed Mar. 2, 1989, now abandoned.

BACKGROUND OF THE INVENTION

The present invention relates to a leukocyte separator and a method of manufacturing the same, and more particularly to a leukocyte separator having a high and stable trapping capability for trapping leukocytes without the danger of discharging foreign material and a method of manufacturing such a leukocyte separator.

Forms of blood transfusion range from conventional whole blood transfusion to component transfusion that is widely relied upon recently by which only a blood component required by a patient is transfused to the patient. In the component transfusion, it is important that desired blood portions or components be separated highly purely from the blood of a donor.

More specifically, various blood components such as concentrated red cells (CRC), a plasma concentrate (PC), and platelet poor plasma (PPP) are separated from collected or donated blood by a centrifugal separation process. Concentrated red cells thus separated are widely used as a component preparation in administering red cells to patients who need them. Heretofore, concentrated red cells contain many leukocytes and platelets, which should be removed as much as possible. Various efforts have been made for the removal of leukocytes and platelets from donated blood.

A variety of methods are known for increasing the purity of red cell preparations. Such methods include a gravitational and centrifugal separating method utilizing different specific gravities of blood cells, a method using a trapping material for trapping blood cells by sticking, adhesion, or the like, and a method of separating leukocytes by using a red cell coagulant. Among these methods, the method using a trapping material is widely used since it has a high efficiency for leukocytal removal and is easy to carry out. Typical trapping materials include very short fibers such as natural cellulose fibers, polyester fibers, polyamide fibers, polyacrylonitrile fibers, glass fibers, or the like, which are packed in a column, or fabricated into nonwoven fabric.

Where fibers are packed in a column, it is quite difficult, tedious, and time-consuming to fill the fibers uniformly in the column. Dependent on how the fibers are packed, channeling may occur while the trapping material is being handled for purifying red cell preparations. If the fibers are packed in a high density for sufficiently trapping leukocytes, the time required for filtering the blood through the trapping material becomes very long. Some of the packed fibers may flow out of the column during usage since the fibers are not usually intertwined sufficiently. These problems are not liable to occur with those fibers which are fabricated into nonwoven fabric. However, it has been pointed out that a nonwoven fabric used as a trapping material is apt to get easily clogged by blood cells trapped by the fabric.

SUMMARY OF THE INVENTION

It is a major object of the present invention to provide a leukocyte separator which has a high and stable trapping capability for trapping leukocytes, is capable of separating leukocytes efficiently from blood, is free from clogging and channeling due to trapped leukocytes during usage, and also from the danger of discharging fibers and other foreign material, and a method of manufacturing such a leukocyte separator.

Another object of the present invention is to provide a leukocyte separator for trapping and separating leukocytes from blood, said leukocyte separator being made of a porous material having a bubble point ranging from 0.08 to 0.3 $kg/cm^2$ and a thickness of at least 0.30 mm.

Still another object of the present invention is to provide a leukocyte separator wherein said bubble point ranges from 0.13 to 0.25 $kg/cm^2$.

Yet another object of the present invention is to provide a leukocyte separator wherein said thickness is at least 0.5 mm.

Yet still another object of the present invention is to provide a leukocyte separator wherein said porous material comprises polyvinyl alcohol.

A further object of the present invention is to provide a leukocyte separator wherein said porous material comprises polyurethane foam.

A still further object of the present invention is to provide a method of manufacturing a leukocyte separator for trapping and separating leukocytes from blood, said method comprising the step of pressing a porous material having a bubble point smaller than 0.13 $kg/cm^2$ to produce a porous material having a thickness of at least 0.3 mm and a bubble point ranging from 0.13 to 0.3 $kg/cm^2$.

A yet further object of the present invention is to provide a method of manufacturing a leukocyte separator, further comprising the step of holding said first-mentioned porous material under a pressure of about 400 $kg/cm^2$ at a temperature of about 80° C. for about 3 minutes.

The above and other objects, features and advantages of the present invention will become more apparent from the following description when taken in conjunction with the accompanying drawings in which a preferred embodiment of the present invention is shown by way of illustrative example.

DETAILED DESCRIPTION OF THE PREFERRED EMBODIMENT

A leukocyte separator according to the present invention is used in selectively separating only leukocytes from a fluid containing leukocytes and red cells through a filtering process. In devising the leukocyte separator of the invention, the inventor checked a filter product made of a commercially available porous material such as of polyvinyl alcohol, for example, and a filter product made of a polyurethane foamed material (which is a porous material) for a bubble point, the membrane thickness of a leukocyte separator, a leukocyte separating ability, and uniformness of pore diameters.

The term "bubble point" is well known in the field of filters of porous materials, and means an air pressure for forcing air through completely wet pores in a filter. For example, a membrane filter has minute and uniform passages like capillaries extending from one side to the other. A bubble point test conducted on the membrane filter measures the diameter of the passages by knowing a minimum pressure (bubble point) required to force a liquid that has been retained in the passages due to surface tension out of the passages. More specifically, water is held in contact with one side of the membrane filter to wet the filter side and air pressure applied to the other side of the membrane filter is progressively increased. When small successive air bubbles passing through the filter are observed, the air pressure applied to the other side of the filter is measured as a bubble point.

Figure 1:
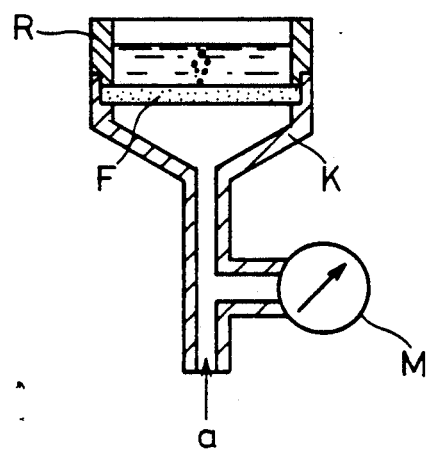
FIG. 1 is a cross-sectional view of a device for measuring a bubble point.

A bubble point may be measured using an experimental device as shown in FIG. 1. A filter F to be measured for a bubble point is horizontally placed on a step in an upper larger-diameter end of an air feed pipe K, and secured in pace by a presser ring R threaded into the larger-diameter portion of the air feed pipe K. A manometer M is attached to a branch pipe extending from the air feed pipe K below the larger-diameter portion thereof. For measurement, water is held on the upper surface of the filter F, and a negative pressure is applied to the filter F to replace air in the filter F with water. Air is then supplied into the air feed pipe K from its lower end while the pressure of air is being progressively increased. The indication of the manometer M the instant small successive air bubbles start emerging from the upper surface of the filter F is measured as a bubble point. The bubble point depends upon the diameter of the passages or pores in the porous filter and also various surface conditions of the porous material of the filter such as electric charges and hydrophilic nature of the porous material.

The leukocyte separator according to the present invention has an excellent leukocyte separating ability defined by a limited range of bubble points and a limited minimum thickness of the separator. More specifically, where leukocytes are to be separated by a filtering process, it is inadequate to define a leukocyte separating ability simply with the size of pores in a leukocyte separator (filter) because of different blood cell sizes, deformabilities, and sticking or adhesion capabilities with respect to foreign material, but it is suitable to define such a leukocyte separating ability with the magnitude of bubble points. Moreover, since many blood cells are suspended in blood, in order to trap leukocytes efficiently and durably, it is not preferable to define a leukocyte separating ability solely with bore diameters, but a leukocyte separating ability should be defined by a thickness range of the separator in combination with the bubble point range.

From this point of view, the inventor has experimentally confirmed that a trapping space for efficiently removing leukocytes can be produced by using as a leukocyte separator a porous material having a bubble point ranging from 0.08 to 0.30 kg/cm$^2$ and a thickness of at least 0.30 mm. The leukocyte separating efficiency of the leukocyte separator is particularly good when the bubble point is in the range of from 0.13 to 0.25 kg/cm$^2$.

It has been confirmed that the leukocyte separating efficiency would be lowered if the bubble point were less than 0.08 kg/cm$^2$. If the bubble point were higher than 0.3 kg/cm$^2$, then almost no blood flow would be produced, and excessive pressurization on the blood to cause a blood flow would damage blood cells when separating them from the blood.

Even when the bubble point ranges from 0.08 to 0.30 kg/cm$^2$, the leukocyte separating efficiency would be poor if the thickness of the separator were less than 0.30 mm. This appears to result from a reduced frequency of contact between the separator and leukocytes. If the thickness of the separator were smaller than 0.30 mm, the separator might be deformed under the pressure of blood flowing through the separator. The separator thickness less than 0.30 mm is not preferable also because the mechanical strength of the separator is low. The separator thickness of 0.50 mm or more can provide sufficient leukocyte separating efficiency and mechanical strength.

The porosity of the separator is preferably in the range of from 50 to 90%. If the porosity were lower than 50%, then the rate of processing blood would be low, and if the porosity were higher than 90%, then the mechanical strength of the separator would be low.

While it has heretofore been pointed out that difficulty is experienced in manufacturing a separator having a bubble point ranging from 0.13 to 0.30 kg/cm$^2$ and a uniform pore diameter, it is possible to manufacture a separator having a uniform pore diameter according to a manufacturing method of the present invention. Such a separator is preferable because it can prevent clogging and channeling due to trapped leukocytes when separating the leukocytes.

The leukocyte separator according to the present invention can be manufactured from synthetic rubber,, thermoplastic resin, thermosetting resin, and porous material. It is particularly preferable to employ a porous material of polyvinyl alcohol, e.g., "BELL-ETA A-3160" (Registered trademark in Japan, manufactured by Kanebo, Ltd.) or a porous material of polyurethane foam, e.g., "RUBYCELL" (Registered trademark in Japan, manufactured by Toyo Polymer, Ltd.) to keep the bubble point in the range of from 0.08 to 0.30 kg/cm$^2$.

However, the material of the leukocyte separator of the invention is not limited as it has no effect on the blood it processes and insofar as the thickness of the separator is at least 0.30 mm and the separator has a bubble point ranging from 0.08 to 0.30 kg/cm$^2$ and provides a space for trapping leukocytes.

The inventor has thought that a desired separator may be fabricated by pressing a porous material having a large pore diameter, in view of the fact that large pore diameters can easily be controlled so as to be uniform. When a porous material is pressed, its pores are flattened. Therefore, if the minor diameter of the flattened pores can be controlled so as to be appropriately smaller than the diameter of leukocytes to be trapped, then the pressed porous material can be altered into a separator having a suitable leukocyte trapping ability. However, it is difficult to detect whether the minor diameter of the flattened pores of the pressed porous material is appropriately smaller than the diameter of leukocytes to be trapped. The inventor has then thought of utilizing the measurement of a bubble point for the control of a pressure for pressing the porous material.

More specifically, a porous material having a bubble point of 0.101 kg/cm$^2$ and a thickness of 2.0 mm was selected from commercially available porous materials of polyvinyl alcohol, and was pressed into various thicknesses under the pressure of 400 kg/cm$^2$ at 80° C. for 3 minutes.

Figure 2:
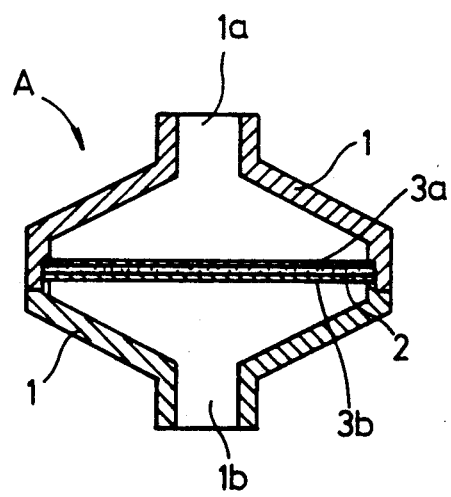
FIG. 2 is a cross-sectional view of a leukocyte separating device which employs a leukocyte separator according to the present invention.
Figure 3:
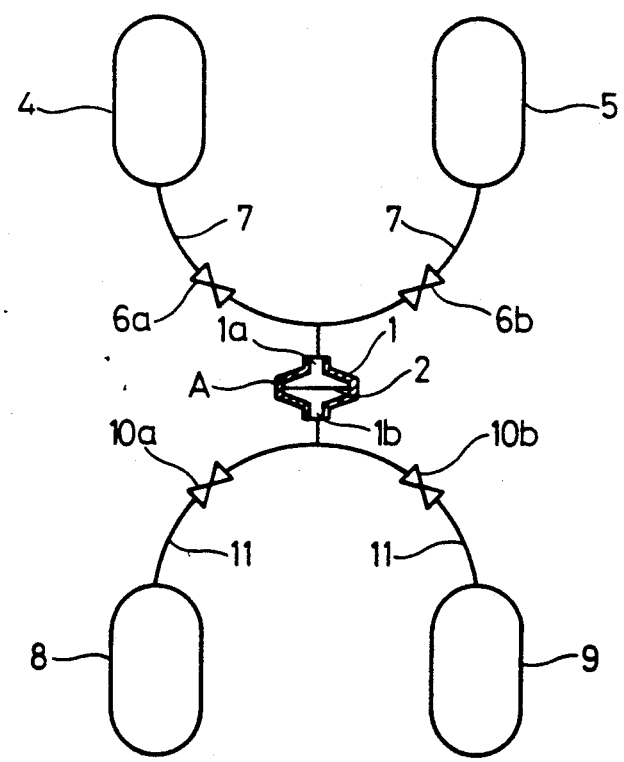
FIG. 3 is a schematic diagram of a leukocyte separating circuit employing the leukocyte separating device shown in FIG. 2.

Leukocyte separators of the invention thus manufactured and conventional comparative leukocyte separators were assembled in a leukocyte separating device A shown in FIG. 2, and gut in a leukocyte separating circuit B shown in FIG. 3 for leukocyte removal efficiency tests.

In FIG. 2, the leukocyte separating device A includes a housing 1 having a blood inlet 1a in its upper end and a blood outlet 1b in its lower end and divisible into upper and lower housing members. A leukocyte separator 2 of the invention is horizontally held in the housing 1 by support members 3a, 3b and divides the space in the housing 1 into upper and lower chambers.

As shown in FIG. 3, the leukocyte separating circuit includes a blood bag 4 for containing blood to be processed and a physiological saline bag 5 for containing a physiological saline, the bags 4, 5 being positioned above the leukocyte separating device A. The bags 4, 5 have fluid outlets connected to the blood inlet 1a of the leukocyte separating device A through a pair of bifurcated conduits 7 having clamps 6a, 6b respectively thereon.

The leukocyte separating circuit also includes a blood collecting bag 8 for collecting processed blood and a physiological saline collecting bag 9 for collecting the physiological saline, the bags 8, 9 being positioned below the leukocyte separating device A. The bags 8, 9 have fluid inlets connected to the blood outlet 1b of the leukocyte separating device A through a pair of bifurcated conduits 11 having clamps 10a, 10b respectively thereon.

A process of separating leukocytes from blood is carried out as follows: The clamps 6b, 10b are opened and the clamps 6a, 10a are closed to allow the physiological saline to flow from the physiological saline bag 5 into the leukocyte separating device A to prime the same. The physiological saline which flows down through the leukocyte separating device A is collected into the physiological saline collecting bag 9. After the leukocyte separating device A has been primed, the clamps 6b, 10b are closed and the clamps 6a, 10a are opened to allow the blood to flow from the blood bag 4 into the leukocyte separating device A. When the blood passes through the leukocyte separator 2 in the leukocyte separating device A, leukocytes are trapped and separated from the blood by the leukocyte separator 2. The blood from which the leukocytes have been removed is then collected into the blood collecting bag 8.

After all the blood has been discharged from the blood bag 4, the clamp 6a is closed, and the clamp 6b is opened again in order to collect any blood remaining in the leukocyte separating device A. The physiological saline is supplied again into the leukocyte separating device A to force the remaining blood out of the leukocyte separating device A into the blood collecting bag 8. After the remaining blood has been collected, the clamp 10a is closed, and the clamp 10b is opened to collect the physiological saline, which was used to collect the remaining blood, into the physiological saline collecting bag 9.

Through the above process, the leukocytes are trapped and separated in the leukocyte separating device A, more precisely, the leukocyte separator 2 of the invention.

The results of the leukocyte removal efficiency tests conducted on the various leukocyte separators 2 having different bubble points and thicknesses and assembled in the leukocyte separating circuit are indicated on Tables 1 through 3 below.

TABLE 1

| Bubble point (kg/cm²) | Membrane thickness (mm) | WBC REM (%) |
|---|---|---|
| Inventive example | | |
| 1 | 0.160 | 0.30 | 97 |
| 2 | 0.132 | 1.50 | 95.5 |
| 3 | 0.140 | 1.00 | 98.8 |
| 4 | 0.154 | 0.80 | 99.0 |
| 5 | 0.140 | 0.50 | 90.1 |
| Comparative example | | |
| 1 | 0.140 | 0.20 | 33 |

TABLE 2

| Bubble point (kg/cm²) | Membrane thickness (mm) | WBC REM (%) |
|---|---|---|
| Inventive example | | |
| 6 | 0.150 | 0.60 | 80 |
| 7 | 0.199 | 1.5 | 100 |
| 8 | 0.215 | 0.3 | 95 |
| Comparative example | | |
| 2 | 0.076 | 1.0 | 20 |
| 3 | 0.150 | 0.2 | 25 |

TABLE 3

| Bubble point (kg/cm²) | Membrane thickness (mm) | WBC REM (%) |
|---|---|---|
| Pressed separator | | |
| 1 | 0.154 | 0.8 | 99 |
| 2 | 0.140 | 1.0 | 98.8 |
| 3 | 0.132 | 1.5 | 95.5 |
| Unpressed separator | | |
| 1 | 0.101 | 2.0 | 75.0 |

WBC REM (%) in Tables 1 through 3 above represents the leukocyte removal efficiency and was determined by counting leukocytes suspended in the blood before and after the leukocytal separation, with BLT-8 (manufactured by Ortho Diagnostic Inc.). The membrane thickness of the leukocyte separator 2 was measured when it was dry.

The leukocyte separator according to each of the inventive and comparative examples in Table 1 was made of a porous material of polyvinyl alcohol, e.g., "BELL-ETA A-3160", whereas the leukocyte separator according to each of the inventive and comparative examples in Table 2 was made of a porous material of polyurethane foam.

Table 3 shows, for comparison, the results of the tests on pressed leukocyte separators 2 which were fabricated by pressing a porous material of polyvinyl alcohol according to the present invention and an unpressed leukocyte separator. The pressed separators 1, 2, and 3 in Table 3 are the same as the inventive separators 4, 3, and 2, respectively, in Table 1.

As shown in Table 3, the leukocyte separators 2 produced by pressing a porous material have a leukocyte removal efficiency higher than that of the unpressed leukocyte separator. The leukocyte removal efficiency tests described above indicate that the leukocyte separator of the invention was free of clogging and channeling which would otherwise result from trapped leukocytes and did not discharge fibers and other foreign matter. Accordingly, it was confirmed that he leukocyte separator 2 produced according to the manufacturing process of the present invention has a high and stable ability to trap leukocytes.

As described above, a leukocyte separator 2 having a bubble point ranging from 0.13 to 0.30 kg/cm$^2$, a thickness of at least 0.30 mm, and a high leukocyte removal efficiency can be produced by pressing a porous material having a bubble point less than 0.13 kg/cm$^2$ and a predetermined thickness.

As described above, the leukocyte separator according to the present invention can trap and remove leukocytes efficiently from blood through a simple operation. Since the leukocyte separator of the invention is made of a porous material, it does not discharge fibers or the like into the blood being processed thereby. When a leukocyte separating device is to be manufactured using the leukocyte separator of the invention, the leukocyte separator can easily be placed in the housing of the leukocyte separating device.

The manufacturing method of the invention can easily manufacture a leukocyte separator which can trap and remove leukocytes efficiently from blood through a simple operation, prevents clogging and channeling which would otherwise be caused by trapped leukocytes, and does not discharge fibers or other foreign matter into the blood being processed.

Although a certain preferred embodiment has been shown and described, it should be understood that many changes and modifications may be made therein without departing from the scope of the appended claims.

What is claimed is:

1. A leukocyte separator for trapping and separating leukocytes from blood, said leukocyte separator being made of a porous foamed plastic having a bubble point ranging from 0.08 to 0.3 kg/cm$^2$ and a thickness of at least 0.30 mm.

2. A leukocyte separator according to claim 1, wherein said bubble point ranges from 0.13 to 0.25 kg/cm$^2$.

3. A leukocyte separator according to claim 1, wherein said thickness is at least 0.5 mm.

4. A leukocyte separator according to claim 1, wherein said porous material comprises polyvinyl alcohol.

5. A leukocyte separator according to claim 1, wherein said porous material comprises polyurethane foam.

6. A leukocyte separator according to claim 1 wherein the porosity thereof ranges from 50% to 90%.

7. A leukocyte separator according to claim 1, wherein said porous foamed plastic material is manufactured from synthetic rubber, thermoplastic resin, or thermosetting resin.

* * * * *